United States Patent [19]
Steinbach et al.

[11] Patent Number: 4,855,129
[45] Date of Patent: Aug. 8, 1989

[54] SKIN-PROTECTING OR SKIN-CARE COMPOSITION

[75] Inventors: Hans-Horst Steinbach, Bergisch Gladbach; Bernd Wittmann, Odenthal, both of Fed. Rep. of Germany

[73] Assignee: Bayer Aktiengesellschaft, Leverkusen, Fed. Rep. of Germany

[21] Appl. No.: 117,271

[22] Filed: Nov. 5, 1987

[30] Foreign Application Priority Data

Nov. 25, 1986 [DE] Fed. Rep. of Germany ....... 3640177

[51] Int. Cl.$^4$ .............................................. A61K 7/021
[52] U.S. Cl. ........................................ 424/63; 424/63; 424/78; 106/287.13; 106/287.15
[58] Field of Search ............................. 424/59, 63, 78; 106/287.13, 287.15

[56] References Cited

U.S. PATENT DOCUMENTS

| | | | |
|---|---|---|---|
| 4,355,046 | 10/1982 | Süess | 424/59 |
| 4,425,364 | 1/1984 | Vanlerberghe | 424/59 |
| 4,563,346 | 1/1986 | Deckner | 424/59 |

FOREIGN PATENT DOCUMENTS

| | | | |
|---|---|---|---|
| 0142830 | 5/1985 | European Pat. Off. | |
| 0197485 | 10/1986 | European Pat. Off. | |
| 0200916 | 11/1986 | European Pat. Off. | |
| 3010572 | 9/1981 | Fed. Rep. of Germany | 424/59 |

OTHER PUBLICATIONS

"Formulation Ideas", 694 Soap, Cosmetics, Chemical Specialties, vol. 58, (1982), Sep., No. 9, NY NY USA, pp. 81 and 82.

*Primary Examiner*—Thurman K. Page
*Assistant Examiner*—P. L. Prater
*Attorney, Agent, or Firm*—Sprung Horn Kramer & Woods

[57] ABSTRACT

A skin care or skin-protecting composition comprising a highly viscous polydimethylsiloxane which optionally contains OH, vinyl, phenyl or alkyl groups with 2 to 6 C atoms in the terminal and/or middle positions, the polydimethylsiloxane having a viscosity of $10^6$ to $5\times10^7$ mPa.s, and a highly volatile, linear or cyclic siloxane.

11 Claims, No Drawings

SKIN-PROTECTING OR SKIN-CARE COMPOSITION

The present application relates to a composition which is suitable as skin protection, in particular for the hands.

Skin protection agent—specifically for protection of the hands from contamination and chemicals, as well as mechanical stress—are known in various compositions, e.g., creams or lotions.

Such creams or lotions are usually based on polydimethylsiloxane or on derivatives or copolymers of this silicone polymer, in some cases water-soluble resins, acrylates, carboxyvinyl polymers, vinyl acetate, vinylpyrrolidone and waxes are used as film-forming agents or thickeners.

Apart from silicones (polydimethylsiloxanes and volatile silicones), glycerol is used as a care component. Surfactants are used as emulsifying/homogenizing agents.

The protective creams and lotions obtainable on the market in this respect are improved by the measures according to the invention with regard to a sufficiently stable protective film. Preconditions for the correct functioning of the protective film are its adequate ease of distribution, film thickness, lubricating properties and abrasion stability. It has been found that as the viscosity of the polydimethylsiloxane increases, the skin protection is improved, but working in is worsened. The use of polydimethylsiloxanes with viscosities of between 10 and 1,000 mPa.s has therefore become accepted. It has now been found that these properties and significantly improved by the active compound combinations described here, which are formulations.

Within the abundant supply of film-forming silicones, essential improvements in the film stability can be achieved by a procedure in which solutions of very highly viscous polydimethylsiloxanes are dissolved in volatile low-polymeric linear or cyclic siloxanes and these solutions are emulsified or incorporated in fine division to the extent of 10–40%, preferably, in commercially available hand creams (oil-in-water system). The combination of such a solution of different polysiloxanes has the advantage of being easier to distribute on the skin. After the volatile compounds have evaporated off, a protective film with good adhesive, low wear properties and good separation properties is obtained. The protective film consisting of highly viscous polydimethylsiloxane also repels water and dirt.

The present invention thus relates to a skin care or skin-protecting composition, characterized in that it contains highly viscous polydimethylsiloxanes, which optionally contain OH, vinyl, phenyl or alkyl groups with 2 to 6 C atoms in the terminal and/or middle positions and have a viscosity of $10^6$ to $5\times 10^7$ mPa.s, and highly volatile, linear or cyclic siloxanes.

The contents of methyl-vinyl-siloxy groups are, for example, between 200 ppm and 20% by weight, and the contents of OH—$Me_2$—$SiO_{\frac{1}{2}}$ are between 100 and 1,000 ppm. The ratio of phenyl groups to methyl groups is in the range from 1:2.2 to 1:5.1.

These highly viscous polydimethylsiloxanes can be dissolved in volatile cyclic or linear dimethylsiloxanes in customary mixing units, such as shaking machines, dissolvers, planetary mixers and kneaders. Hexamethyldisiloxane, octamethylcyclotetrasiloxane and decamethylcyclopentasiloxane have proved particularly suitable as physiologically acceptable low-viscosity siloxane solvents. 10 to 40% strength solutions of these highly viscous polydimethylsiloxanes in volatile, cyclic or linear dimethylsiloxanes have viscosities of 300 to 100,000 mPa.s and can easily be incorporated into commercially available hand creams. The concentration of the active compound combination in commercially available hand creams can be between 10 and 50%. An addition of about 40% has proved to be quite favorable for the preparation of a "liquid glove".

Corresponding compositions according to the invention thus have a content of highly viscous polydimethylsiloxane of about 5 to 20% by weight, preferably 8 to 15% by weight, and a content of 10 to 50% by weight, preferably 20 to 40% by weight, of highly volatile siloxanes—based on the total composition.

It should be emphasized that after washing skin protected with the "liquid glove", a thin protective care film remains on the skin, which also subsequently still protects the skin from attack by, for example, oil and chemicals.

The active compound combination to be employed according to the invention can be prepared as follows, on the basis of the recipes given below:

The corresponding amount of the polymer is introduced into the volatile siloxane present in a kneader, planetary mixer or dissolver. Since the volatile siloxanes used are combustible, it is advisable to pass an inert gas (for example nitrogen) over throughout the entire solution period. Because of the high volatility, stirred vessels and kneaders should as far as possible be closed and the inert gas should be passed over at a low flow rate.

Typical recipes such as are used according to the invention are, for example, as follows (% data are % by weight):

The content of methyl-vinyl groups in the highly viscous polydimethylsiloxane mentioned in the recipes is 0.1% by weight.

(1) 20% of highly viscous polydimethylsiloxane containing vinyl groups (viscosity about 18,000,000 mPa.s) and 80% of octamethylcyclotetrasiloxane (2) 20% of highly viscous polydimethylsiloxane containing vinyl groups (viscosity about 18,000,000 mPa.s) and 80% of decamethylcyclopentasiloxane (3) 20% of highly viscous polydimethylsiloxane containing vinyl groups (viscosity about 19,000,000 mPa.s) and 80% of hexamethyldisiloxane (4) 25% of highly viscous polydimethylsiloxane containing vinyl groups (viscosity about 18,500,000 mPa.s) and 75% of octamethylcyclotetrasiloxane (5) 25% of highly viscous polydimethylsiloxane containing vinyl groups (viscosity about 31,200,000 mPa.s) and 75% of decamethylcyclopentasiloxane (6) 25% of highly viscous polydimethylsiloxane containing vinyl groups (viscosity about 18,000,000 mPa.s) and 75% of hexamethyldisiloxane (7) 30% of highly viscous polydimethylsiloxane containing vinyl groups (viscosity about 45,100,000 mPa.s) and 70% of octamethylcyclotetrasiloxane (8) 30% of highly viscous polydimethylsiloxane containing vinyl groups (viscosity about 18,800,000 mPa.s) and 70% of decamethylcyclopentasiloxane (9) 30% of highly viscous polydimethylsiloxane containing vinyl groups (viscosity about 39,600,000 mPa.s) and 70% of hexamethyldisiloxane

(10) 40% of highly viscous polydimethylsiloxane containing vinyl groups (viscosity about 27,100,000 mPa.s) and 60% of octamethylcyclotetrasiloxane

(11) 40% of highly viscous polydimethylsiloxane containing vinyl groups (viscosity about 48,000,000 mPa.s) and 60% of decamethylcyclopentasiloxane
(12) 40% of highly viscous polydimethylsiloxane containing vinyl groups (viscosity about 18,500,000 mPa.s) and 60% of hexamethyldisiloxane
(13) 20% of highly viscous polydimethylsiloxane containing terminal OH groups (viscosity about 14,000,000 mPa.s) and 80% of octamethylcyclotetrasiloxane
(14) 20% of highly viscous polydimethylsiloxane containing terminal OH groups (viscosity about 30,500,000 mPa.s) and 80% of decamethylcyclopentasiloxane
(15) 20% of highly viscous polydimethylsiloxane containing terminal OH groups (viscosity about 25,000,000 mPa.s) and 80% of hexamethyldisiloxane
(16) 25% of highly viscous polydimethylsiloxane containing terminal OH groups (viscosity about 41,700,000 mPa.s) and 75% of octamethylcyclotetrasiloxane
(17) 25% of highly viscous polydimethylsiloxane containing terminal OH groups (viscosity about 16,000,000 mPa.s) and 75% of decamethylcyclopentasiloxane
(18) 25% of highly viscous polydimethylsiloxane containing terminal OH groups (viscosity about 16,000,000 mPa.s) and 75% of hexamethyldisiloxane
(19) 30% of highly viscous polydimethylsiloxane containing terminal OH groups (viscosity about 35,500,000 mPa.s) and 70% of octamethylcyclotetrasiloxane
(20) 30% of highly viscous polydimethylsiloxane containing terminal OH groups (viscosity about 27,000,000 mPa.s) and 70% of decamethylcyclopentasiloxane
(21) 30% of highly viscous polydimethylsiloxane containing terminal OH groups (viscosity about 17,000,000 mPa.s) and 70% of hexamethyldisiloxane
(22) 40% of highly viscous polydimethylsiloxane containing terminal OH groups (viscosity about 37,100,000 mPa.s) and 60% of octamethylcyclotetrasiloxane
(23) 40% of highly viscous polydimethylsiloxane containing terminal OH groups (viscosity about 15,000,000 mPa.s) and 60% of decamethylcyclopentasiloxane
(24) 40% of highly viscous polydimethylsiloxane containing terminal OH groups (viscosity about 46,500,000 mPa.s) and 60% of hexamethyldisiloxane Very good incorporation of the active compound combination is achieved at viscosities in the range from 10,000 to 20,000 mPa.s An optimum of desired properties is obtained with a combination of 25% of the highly viscous polydimethylsiloxane containing terminal OH groups with 75% of volatile siloxane. Higher concentrations lead to the same phenomenon as with the combination of 40% of polydimethylsiloxane containing vinyl groups with 60% of volatile siloxanes. The following viscosities have been measured for the various solutions of polymers containing OH groups or vinyl groups in volatile siloxanes:

| % of OH polymer | % of volatile siloxane | Viscosity (mPa.s) | % of vinyl polymer | % of volatile siloxane | Viscosity (mPa.s) |
|---|---|---|---|---|---|
| 10 | 90 | 631 | 10 | 90 | 391 |
| 20 | 80 | 14,750 | 20 | 80 | 5,100 |
| 25 | 75 | 28,600 | 25 | 75 | 14,600 |
| 30 | 70 | 45,530 | 30 | 70 | 26,700 |
| 40 | 60 | 38,800 | 40 | 60 | 92,400 |

The compositions according to the invention can be incorporated into any desired creams or lotions. Hand cream compositions are particularly suitable, but the subject-matter of the invention is in no way restricted to these.

The invention may be illustrated in more detail with the aid of the following examples:

EXAMPLE 1

25% by weight of an active compound combination consisting of 25% by weight of polydimethylsiloxane containing vinyl groups (viscosity about 25,000,000 mPa.s) and 75% by weight of octamethylcyclotetrasiloxane were admixed to 75% by weight of a standard hand cream.

The standard hand cream was prepared from: (a) 8.30% by weight of cetylstearyl alcohol, 2.00% by weight of cetylstearyl alcohol oxyethylated with about 10 mol of ethylene oxide, 5.00% by weight of fatty acid mono- and diglyceride, 3.00% by weight of decyl oleate, 3.00% by weight of polydimethylsiloxane (350 mPa.s) and 0.05% by weight of propyl p-hydroxybenzoate and (b) 51.90% by weight of distilled water, 0.15% by weight of methyl p-hydroxybenzoate, 25.00% by weight of glycerol DAB 7, 1.00% by weight of sodium cetylstearyl sulphate, 0.20% by weight of 5-ureidohydantoin and 0.40% by weight of perfume oil.

EXAMPLE 2

40% by weight of an active compound combination consisting of 25% by weight of a polydimethylsiloxane containing vinyl groups (vinyl group content about 900 ppm) and with a viscosity of about 21,000,000 mPa.s and 75% by weight of octamethylcyclotetrasiloxane were added to 60% by weight of a commercially available hand cream (Stokolan ® from Stockhausen).

These experimental recipes led to good results in respect of ease of incorporation of the active compound combination chosen as well as ease of application and functional properties.

The optimum proved to be a mixture of 40% of an active compound combination consisting of 25% of a polydimethylsiloxane containing terminal OH groups and 75% of a volatile siloxane (octamethylcyclotetrasiloxane) and 60% of a commercially available hand cream.

It has been found that as the viscosity of the polymer used increases, the life of the protective film after washing the hands and the dirt-repellant properties are improved.

Depending on the activity to be undertaken, the hands should be washed between the start of work and the breaks or the end of work and new "liquid glove" should be applied, and in particular by distributing a sufficient amount thoroughly over the inside and outside surfaces of the hands in the usual way. It should be ensured that sufficient cream also gets under the fingernails.

The hands can be washed with a commercially available soap or liquid soap. The use of special soap or hand-washing paste, which are known to remove fat from the skin and make it chapped and cracked, is unnecessary.

The skin-protective action was tested against isopropanol in the field of clinical disinfection of the hand. In an orientating test, the ease of washing of cream-covered felt-tip pen markings on the skin was tested. After the hands had been washed several times, the hands treated with the liquid glove described showed differences striking to the eye in comparison with normal commercially available hand creams.

It will be appreciated that the instant specification and claims are set forth by weay of illustration and not limitation, and that various modifications and changes may be made without departing from the spirit and scope of the present invention.

What is claimed is:

1. A skin care or skin-protecting composition comprising as an active ingredient a highly viscous polydimethysiloxane having a viscosity of $10^6$ to $5 \times 10^7$ mPa.s, and a highly volatile, linear or cyclic siloxane, wherein the content of the highly viscous polydimethylsiloxane is 5 to 20% by weight and the content of the highly volatile siloxane is 10 to 50% by weight, based on the weight of the total composition.

2. A composition according to claim 1, wherein the polydimethylsiloxane contains OH, vinyl, phenyl and-/or $C_2$ to $C_6$ alkyl groups in the terminal and/or middle positions.

3. A composition according to claim 1, wherein content of the highly viscous polydimethylsiloxane is 8 to 15% by weight and the content of the highly volatile siloxane is 20 to 40% by weight, based on the total composition.

4. A composition according to claim 1, wherein the polydimethylsiloxane contains terminal OH groups, the content of the polydimethylsiloxane of the active ingredient is 25% by weight and the content of the volatile siloxane of the active ingredient is 75% by weight, based on the weight of the total composition.

5. A composition according to claim 1, wherein the polydimethylsiloxane contains vinyl groups, the content of the polydimethylsiloxane of the active ingredient is 40% by weight and the content of the volatile siloxane of the active ingredient is 60% by weight, based on the weight of the total composition.

6. A composition according to claim 2, wherein said alkyl group is a methyl group.

7. A composition according to claim 6, wherein the content of the methyl-vinyl-siloxy group is 200 ppm to 20% by weight.

8. A composition according to claim 6, wherein the content of $OH-Me_2-SiO_{\frac{1}{2}}$ is 100 to 1,000 ppm.

9. A composition according to claim 6, wherein the ratio of phenyl groups to methyl groups is 1:2.2 to 1:5.1.

10. A composition according to claim 6, wherein the content of methyl-vinyl groups in the highly viscous polydimethylsiloxane is 0.1% by weight.

11. A composition according to claim 1, wherein the highly volatile siloxane is selected from the group consisting of octamethylcyclotrasiloxane, decamethylcyclopentasiloxane and hexamethyldisiloxane.

* * * * *